(12) United States Patent
Al Zuhair et al.

(10) Patent No.: US 12,416,031 B1
(45) Date of Patent: Sep. 16, 2025

(54) SYSTEM AND METHODS FOR CONTINUOUS PRODUCTION OF CYCLODEXTRINS FROM CELLULOSE

(71) Applicant: United Arab Emirates University, Al Ain (AE)

(72) Inventors: Sulaiman Al Zuhair, Al Ain (AE); Saleha Almardeai, Al Ain (AE); Babatunde Ogunbadejo, Al Ain (AE); Emad Elnajjar, Al Ain (AE); Yaser Mohamed Greish, Al Ain (AE); Boguslaw Kruczek, Al Ain (AE); Bart Van Der Bruggen, Al Ain (AE)

(73) Assignee: UNITED ARAB EMIRATES UNIVERSITY, Al-Ain (AE)

( * ) Notice: Subject to any disclaimer, the term of this patent is extended or adjusted under 35 U.S.C. 154(b) by 0 days.

(21) Appl. No.: 18/989,701

(22) Filed: Dec. 20, 2024

(51) Int. Cl.
*C12P 19/18* (2006.01)
*C12N 9/10* (2006.01)
*C12P 19/02* (2006.01)
*C12P 19/04* (2006.01)

(52) U.S. Cl.
CPC ............ *C12P 19/18* (2013.01); *C12N 9/1074* (2013.01); *C12P 19/02* (2013.01); *C12P 19/04* (2013.01); *C12Y 204/01019* (2013.01)

(58) Field of Classification Search
CPC .......... C12P 19/18; C12P 19/02; C12P 19/04; C12N 9/1074; C12Y 204/01019; C12M 27/02; C12M 35/04; C12M 21/04; C12M 23/14; C12M 29/10
USPC ...................................... 435/289.1
See application file for complete search history.

(56) References Cited

U.S. PATENT DOCUMENTS

2013/0040350 A1\* 2/2013 Studer .................... C12M 25/02
435/141

\* cited by examiner

*Primary Examiner* — Michael L Hobbs
(74) *Attorney, Agent, or Firm* — MH2 Technology Law Group, LLP

(57) ABSTRACT

The present invention pertains to novel system and methods for the streamlined and efficient continuous production of cyclodextrins by utilizing lignocellulosic wastes. The system comprises a tubular membrane bioreactor where enzymatic hydrolysis of cellulose into glucose is conducted continuously. The method comprises a first part where cellulose is hydrolyzed to pure glucose and a second part where the pure glucose reacts with to CGTase enzyme to obtain pure cyclodextrins.

8 Claims, 1 Drawing Sheet

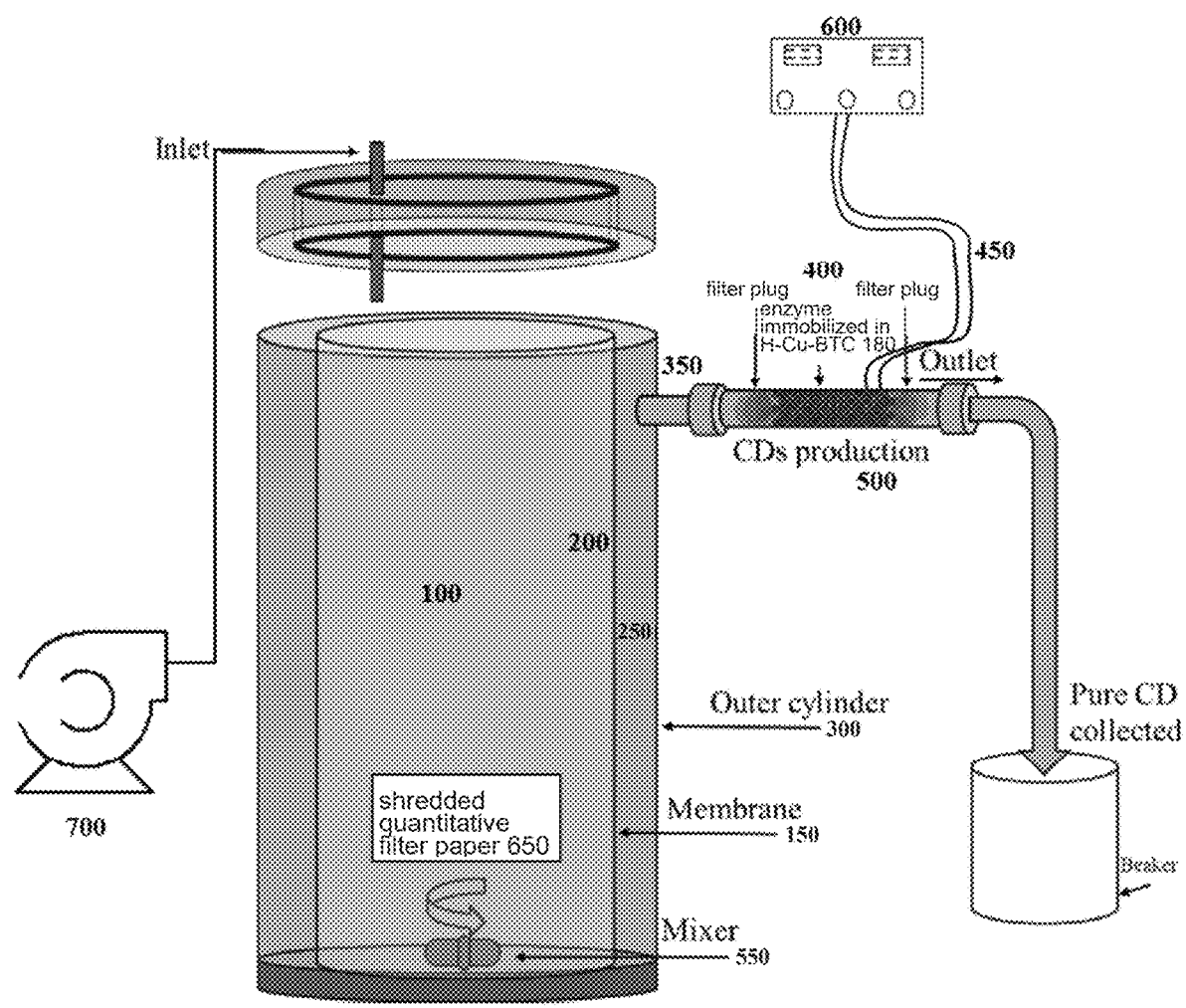

SYSTEM AND METHODS FOR CONTINUOUS PRODUCTION OF CYCLODEXTRINS FROM CELLULOSE

TECHNICAL FIELD

The present invention relates to novel system and methods for streamlined and efficient continuous production of cyclodextrin from lignocellulosic wastes.

BACKGROUND OF THE INVENTION

Cyclodextrins (CDs) are cyclic oligosaccharides composed of six, seven, or eight glucose molecules, known as cyclomaltohexaose (α-CD), cyclomaltoheptaose (β-CD), and cyclomaltooctaose (γ-CD), linked via glycosidic bonds. CDs are crucial in various fields to their ability to form inclusion complexes with diverse molecules [1]. In pharmaceuticals, CDs enhance drug solubility, stability, and bioavailability [2]. In the food industry, they stabilize flavors and vitamins while reducing bitterness [3]. Additionally, CDs have environmental and sustainability benefits, aiding in pollutant removal and the development of eco-friendly pesticides. CDs also find applications in cosmetics, biotechnology, and medicine, primarily due to their hydrophilic and hydrophobic cavities, which allow them to form molecular inclusion complexes with various compounds [4].

CDs are derived through the hydrolysis of starch using cyclodextrin glycosyltransferase (CGTase), which also catalyzes the cyclization of the hydrolyzed glucose [4]. The yield of cyclodextrins (CDs) is primarily influenced by the type and source of starch used, with additional factors such as reaction temperature and pH playing crucial roles in enzyme activity and subsequent CD production outcomes [5]. Various starch-rich biomasses have been explored for CD production, with potato starch being the most widely utilized [6]. In contrast, maize and wheat starch, characterized by low amylopectin and high amylase content, which resulted in less CD compared to other starch biomasses such as cassava has recently attracted attention due to its high amylopectin content [7]. The optimal conditions for CD production vary depending on the form of the CGTase enzyme. For example, free-form CGTase shows the optimum activity at 70° C., whereas immobilization increases thermal stability, with Si-SH-CGTase and Si-NH-G-CGTase exhibiting optimal activity at 80° C. and 90° C., respectively [4].

In addition, CD yield was reported to be significantly affected by the pH, which varies depending on the source of CGTase enzyme. Bacillus ohbensis derived CGTase operates optimally at pH 5.5, while Bacillus sp. CGTase is most active at pH 10 [8-9]. Notably, using Bacillus megaterium derived CGTase with waxy-maize starch achieved up to 91% 13-CD production at 25° C. and pH 7, reflecting its predominant market share among CD types [7, 10]. Conversely, applying CGTase from the same bacterial source to corn starch yields approximately 50% CD production, demonstrating variability compared to other starch derivatives like dextrin, amylase, and amylopectin [11].

The demand for CD is increasing, however, the high production cost is restricting the process [12]. Therefore, different attempts are being investigated to make the process economically feasible. The high production cost is partially attributed to the cost of CGTase enzyme. Using GCTase enzyme in free form is neither yield nor cost efficient, this is because of the high cost of enzyme and the required downstream purification for enzyme separation to be reused [13]. Therefore, enzyme immobilization, in which enzyme is confined onto a support, is favored for enzyme recycling and reusability.

Different supports for CGTase were investigated to enhance the enzyme specific activity, increase the CD production, and retain the enzyme activity for multiple cycles. For example, CGTase was immobilized on graphene nanoplatelets (GNP) and calcium-based two-dimensional metal organic framework (Ca-TMA) [14]. The Ca-TMA showed to result in higher specific activity up to 38 U mg-1 compared to that in the GNP, which was 28 U mg-1, however, the enzyme reusability was enhanced using GNP which retained about 74% of the initial enzyme activity after 8 cycles [14]. On the other hand, recently, industrial agricultural wastes which have high content of starch are an area of research interest to lower down the production cost (rf). For example, the use of cassava bagasse, which is characterized by 50% of starch trapped in the lignocellulose matrix, resulted in around 93 mg CD per enzyme unit with enzyme loading of 2.5 U/g starch for 1 h at 60° C. [11]. The use of lignocellulose waste for CD production should reduce the net cost and have an environmental positive effect as the waste is converted to a high market share product. However, the conversion of cellulose from waste to CD was not investigated previously. Therefore, there is a need for an efficient and continuous production of cyclodextrin.

SUMMARY OF THE EMBODIMENTS

The present invention relates to a novel streamlined and efficient continuous production of cyclodextrin. In one aspect, disclosed herein is a novel system useful for the production of cyclodextrins from lignocellulosic wastes or cellulose. In embodiments, the novel system comprises a tubular biomembrane reactor that comprises an inner reactor, an outer cylinder surrounding the inner reactor, an outlet connecting the outer reactor with a jacketed glass column, and a peristaltic pump connected to the inner reactor, where the system is heated by a tape connected to a thermocouple, in turn connected to a temperature controller. In embodiments, the system comprises a polyethersulfone membrane (PES). The system further comprises a hierarchical copper-based metal-organic framework (H-Cu-BTC), adapted for CGTase enzyme immobilization, and a shredded cellulose substrate.

In a second aspect, disclosed herein is a novel two-parts method utilizing the system of the present invention for the production of CDs from lignocellulosic wastes or cellulose. The present method enables streamlined and efficient continuous production of cyclodextrin. In certain embodiments, the lignocellulosic wastes can be utilized directly for cyclodextrins (CDs) production, unlike other processes which depend only on starch.

In certain embodiments, the method comprises an ultrafiltration process conducted in the inner reactor where the ultrafiltration PES membrane allows for the continuous product separation which passes for CDs production. Therefore, continuous and pure CDs is ensured in this design without further purification units required.

In certain embodiments, the method comprises adding cellulose or lignocellulosic waste and enzymes to the inner reactor, where the cellulose is enzymatically hydrolyzed. In certain embodiments, the glucose produced by the enzymatic hydrolysis through the PES membrane selectively diffuses from the inner reactor to the outer reactor and then to the jacketed glass column. In certain embodiments, the pure glucose reacts with the CGTase enzyme to obtain pure cyclodextrin.

In certain embodiments, the present invention lowers production costs by eliminating the need for additional purification steps and enabling enzyme reusability and promotes a more sustainable production method by optimizing enzyme use and reducing waste.

BRIEF DESCRIPTION OF THE FIGURES

The FIGURE illustrates the design of the membrane bioreactor used for cyclodextrin production.

DETAILED DESCRIPTION OF THE EMBODIMENTS

Definitions

As used in this description and the accompanying claims, the following terms shall have the meanings indicated, unless the context otherwise requires:

As used herein, the singular forms "a", "an", and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising". The transitional terms/phrases (and any grammatical variation thereof) "comprising", "comprises", "comprise", "consisting essentially of", "consisting", and "consists" can be used interchangeably.

The term "exemplary" is used herein to mean "serving as an example, instance, or illustration." Any embodiment described herein as "exemplary" is not necessarily to be construed as preferred or advantageous over other embodiments.

The word "exemplary" is used herein to mean "serving as an example, instance, or illustration." Any embodiment described herein as "exemplary" is not necessarily to be construed as preferred or advantageous over other embodiments.

The present invention pertains to a novel two-parts system and methods for the continuous production of cyclodextrin from cellulose, offering a pure, streamlined, and efficient process. In one aspect, the first part of the system of the present invention comprises a tubular Membrane Bioreactor (MBR) where enzymatic hydrolysis of cellulose into glucose occurs continuously. In certain embodiments, the glucose permeates through an ultrafiltration polyethersulfone (PES) membrane, ensuring that only pure glucose is produced and transported to the second part, eliminating the need for additional purification and downstream processing. In certain embodiments, the second part comprises the continuous stream of pure glucose reacting with the CGTase enzyme in a dedicated reactor, resulting in the production of pure cyclodextrin. In preferred embodiments, the integrated setup significantly reduces the cost of cyclodextrin production by streamlining the process and ensuring high purity at each stage. In certain embodiments, the method of the present invention allows to seamlessly link the two parts, creating an efficient, continuous production cycle.

Additionally, in certain embodiments, the net cost of cyclodextrin production is further reduced through the reusability of the enzymes used in this system. In certain embodiments, in the first part, cellulases are trapped by a polyethersulfone membrane, preventing cellulases from permeating with the glucose to the second part of the system of the present invention. This allows continuous utilization of cellulase for multiple cycles, effectively removing the product inhibition effect. In certain embodiments, in the second part of the present method, the CGTase enzymes are immobilized on a hierarchical copper-based metal-organic framework (H-Cu-BTC), which enhances enzyme stability and reusability.

In certain embodiments, the two-parts system of the present invention includes, but is not limited to, a tubular membrane reactor 100 comprising an inner reactor 200 jacketed by an outer cylinder or reactor 300. In embodiments, the material of the wall of the inner reactor 200 includes, but is not limited to, a polyethersulfone (PES) membrane 150 that has a molecular weight cut-off (MWCO) of about 10 kDa. In certain embodiments, the inner reactor or reaction zone 250 has an internal diameter (ID) of about 10 cm and a height of about 19 cm, and is surrounded by the outer cylinder 300 having an ID of about 15 cm and a height of about 24 cm. In certain embodiments, the outer cylinder 300 comprises an outlet 350 connected to a jacketed glass column 400 having an ID of about 14 mm, a height of about 78 mm, and a total volume of about 8 mL and reaction temperature of enzymatic hydrolysis and cyclodextrins production are 50 and 80° C., respectively.

In another aspect, disclosed herein is a method for the continuous production of cyclodextrins from cellulose or lignocellulosic wastes. In certain embodiments, the method comprises the enzymatic hydrolysis of cellulose performed in the inner reactor or zone 100, where enzymes and substrates are added. In embodiments, pure glucose permeates through the PES membrane 150 while cellulase enzymes and cellulose biomass are selectively restricted to prevent product inhibition and keep the enzymes active. In embodiments, the enzymatic reaction in the inner reactor is agitated at about 450 rpm using a mixer 550 (e.g., magnetic stirrer) to ensure proper mixing. In certain embodiments, the pH of the reaction is adjusted to about pH 5. In embodiments, distilled water is introduced into the inner reaction zone 250 using a peristaltic pump 700 to maintain the reaction at temperature of about 50° C. In certain embodiments, the distilled water, along with the glucose produced, diffuses through the membrane 150 to the outer reactor 300 and then to the jacketed glass column 400. In certain embodiments, the column, where CDs production takes place is loaded with about 0.5 g of CGTase@H-Cu-BTC and maintained at about 80° C. using a heating tape 450 attached to a thermocouple 500 that is in turn connected to a temperature controller 600.

In further embodiments, Whatman® quantitative filter paper (Grade 40) 650 is shredded for use as a standard cellulose substrate for the enzymatic hydrolysis of cellulose. The dimensions of the shredded filter paper are about 5× about 5 mm. In preferred embodiments, the enzymatic hydrolysis of cellulose is carried out at a concentration of cellulose of about 10 g/l and at a water flow of about 0.4 mL/min, with an enzyme concentration of about 0.48 g/l at temperature of about 50° C., at a pH of about 4.8 to 5.0, respectively, and at an agitation speed of about 450 rpm.

In certain embodiments, the H-Cu-BTC is synthesized by mixing solution A with solution B as described in the Examples section below. In certain embodiments, the catalyst is prepared by adding about 0.5 ml of CGTase solution at a concentration of about 1.5 mg/ml to 10 mg H-Cu-BTC to obtain CGTase@H-Cu-BTC.

In preferred embodiments, the CDs production is carried out in the glass column 400 containing about 0.5 g of CGTase@H-Cu-BTC and the glucose stream produced by the enzymatic hydrolysis is continuously fed into the column.

In preferred embodiments, the present invention offers several significant advantages, including a substantial reduction in production costs by eliminating the need for additional purification and downstream processing, and through the reusability of the enzymes involved. Continuous operation ensures a streamlined and efficient cyclodextrin production process, resulting in faster output compared to traditional batch methods. The system guarantees high-purity glucose and cyclodextrin at each stage, enhancing product quality and reducing contamination risks. In addition, the utilization of cellulose from lignocellulosic wastes is an environment friendly method through which a commercially valuable product is produced. Furthermore, the immobilization of CGTase on a hierarchical copper-based metal-organic framework (H-Cu-BTC) and the trapping of cellulases within the PES membrane increase enzyme stability and allow for multiple cycles of use, making the process more sustainable and cost-effective.

EXAMPLES

Example 1—Set-Up Design and Materials and Methods

The two-parts system of the present invention comprises a tubular membrane reactor 100 designed with an inner reactor 200 jacketed by an outer cylinder or reactor 300. The wall of the inner reactor 200 is made of a polyethersulfone (PES) membrane 150 with a molecular weight cut-off (MWCO) of 10 kDa. The inner reaction zone 250, with an internal diameter (ID) of 10 cm and a height of 19 cm, is surrounded by the outer cylinder 300 with an ID of 15 cm and a height of 24 cm. The outlet 350 of the outer cylinder 300 is connected to a jacketed glass column 400 with an ID of 14 mm, a height of 78 mm, and a total volume of 8 mL and a reaction temperature of 80° C.

Enzymatic hydrolysis of cellulose is performed in the inner zone 250, where enzymes and substrates are added. The PES membrane allows glucose to permeate while selectively restricting cellulase enzymes and cellulose biomass, thus preventing product inhibition and keeping the enzymes active. The reaction zone is agitated using a mixer 550 (e.g., magnetic stirrer) at about 450 rpm to ensure proper mixing. Distilled water, maintained at the reaction temperature of about 50° C. and adjusted to about pH 5, is introduced into the inner reaction zone 250 using a peristaltic pump 700. The distilled water, along with the glucose produced, diffuses through the membrane 150 to the outer reactor 300 and then to the jacketed glass column 400. The column, where the CDs production is taking place, is loaded with about 0.5 g of CGTase@H-Cu-BTC and maintained at about 80° C. using a heating tape 450 fitted with a thermocouple 500 connected to a temperature controller 600.

Example 2—Enzymatic Hydrolysis with Product Separation

The enzymatic hydrolysis of cellulose was carried out using Whatman® quantitative filter paper (Grade 40) 650, which was shredded to be used as a standard cellulose substrate, with dimensions of 5×5 mm. The enzymatic hydrolysis of cellulose at a concentration of 10 g/l and a water flow of 0.4 mL/min was carried out with an enzyme concentration of 0.48 g/l at temperature and pH of 4.8, respectively, and an agitation speed of 450 rpm. These conditions were the optimum conditions determined in a previous work using standard cellulose [15] (AI-Mardeai et al., 2022).

Example 3—Catalyst Preparation

The H-Cu-BTC 180 was synthesized according to a previously described method, with some modifications [14] (Ogunbadejo et al., 2024). Briefly, solution A was prepared by dissolving 2.5 mmol of 1,3,5-benzenetricarboxylic acid (H3BTC) in 15 ml of anhydrous methanol. Solution B was prepared by dissolving 4.5 mmol of Cu $(NO_3)_2 \cdot 3H_2O$ in 15 ml of deionized water. To ensure homogeneity, solution B was mixed with solution A and stirred at 150 rpm at 25° C. for 30 min. Subsequently, 6.75 mmol of N, N-dimethylcyclohexylamine were added to the mixture, with the immediate formation of glaucous floccules, showing that the organic amine expedited the synthesis of the MOFs. The glaucous suspension was stirred continuously for 24 h, after which it was filtered, rinsed twice with ethanol, and dried for 12 hr 120° C. in a vacuum oven (DAIHAN SOV-30, Korea). The final product was designated as H-Cu-BTC 180. After which the catalyst was prepared through the addition of 0.5 ml of CGTase solution (Toruzyme® 3.0 L from *Thermoanaerobacter* sp., Novozymes A/S, Bagsvaerd, Denmark) of concentration 1.5 mg/ml to 10 mg H-Cu-BTC 180. The resultant solution was incubated overnight maintained at 25° C. with stirring at 100 rpm in an incubator (Labtech LSB-015S, KOREA) to achieve equilibrium. The supports were collected from the mixture by centrifugation (OHAUS FC5816, USA) at 2290×g for 3 min, and dried at 60° C. for 5 h. The resulting support was designated as CGTase@H-Cu-BTC.

Example 4—Cyclodextrins Production

The CDs production was carried out in the glass column 400 containing 0.5 g of CGTase@H-Cu-BTC. The resultant glucose stream from the enzymatic hydrolysis was continuously fed into the column. The produced CDs were collected at different times and quantified using high performance liquid chromatograph (HPLC) (Prominence, Shimadzu, Japan), equipped with an ultra-amino column (250×4.6 mm, 5 μm, Restek) and refractive index detector (Shimadzu, RID-20A). A mixture of acetonitrile and water (65:35% v/v) was used as the mobile phase at 60° C. with a flowrate of 1 mL/min.

The production of CDs increased steadily throughout the reaction, demonstrating the efficiency of this invention. However, the rate of CD production decreased towards the end of the reaction. This decline is primarily due to the initial single feeding of cellulose for glucose production at the beginning of the reaction. As the reaction progresses, the cellulose degrades and converts to glucose, which then feeds the column where CDs are produced. Towards the end of the reaction, less glucose is fed into the system because the cellulose hydrolysis slows down. This issue can be mitigated by continuously adding cellulose throughout the reaction.

SELECTED EMBODIMENTS

Embodiment 1. A system for continuous production of cyclodextrins from cellulose or lignocellulosic waste, comprising:

a tubular membrane reactor 100 comprising:
  (a) an inner reactor 200;
  (b) an outer cylinder 300 surrounding the inner reactor 200;
  (c) an outlet 350 connecting the outer reactor with a jacketed glass column 400;
  (d) a peristaltic pump 700 connected to the inner reactor 200;
  (e) a heating tape 450 fitted with a thermocouple 500 connected to a temperature controller 600;
  (f) a hierarchical copper-based metal-organic framework (H-Cu-BTC) 180; and
  (g) a quantitative filter paper (Grade 40) 650 shredded into standard cellulose substrate having dimensions of about 5×5 mm,
wherein the inner reactor comprises a polyethersulfone (PES) membrane 150,
wherein the inner reactor 200 is designed for the addition of enzymes, substrates, and lignocellulosic wastes,
wherein the H-Cu-BTC 180 is adapted for CGTase enzyme immobilization, and
wherein the system is useful for the production of cyclodextrins from lignocellulosic wastes or cellulose.

Embodiment 2. The system, wherein the PES membrane 150 has a weight cut-off of about 10 KDa.

Embodiment 3. The system of embodiment 1, which is scalable, wherein the inner reactor 200 has an internal diameter of about 10 cm and a height of about 19 cm. The internal diameter can range from 5 to 50 cm, and the height can range from 10 to 100 cm, depending on the specific application and processing capacity required. For example, in small-scale laboratory setups, the inner reactor dimensions might be closer to the lower range, whereas industrial-scale reactors would utilize the upper end of the range to handle larger volumes and higher throughput.

Embodiment 4. The system of any of the preceding embodiments, which is also scalable, wherein the outer cylinder 300 has an internal diameter of about 15 cm and a height of about 24 cm. The internal diameter of the outer cylinder can range from 10 to 60 cm, and the height can range from 15 to 120 cm. This scalability ensures the system can be adapted to varying process requirements, such as larger heat exchange areas for industrial processes or compact setups for research purposes.

Embodiment 5. The system, of any of the preceding embodiments, wherein the jacketed glass column 400 has an internal diameter of about 14 mm, a height of about 78 mm, and a total volume of about 8 mL, is designed for small-scale and precision applications. For scalability, the internal diameter of the column can range from 10 to 50 mm, the height can range from 50 to 300 mm, and the total volume can range from 5 to 500 mL. These ranges are suitable for scaling up batch or continuous processes where precise control of temperature or reaction conditions is required.

Embodiment 6. A method for using the system of embodiment 1 for cyclodextrin production, wherein the method comprises:
  (a) obtaining cellulose or lignocellulosic waste;
  (b) adding the cellulose to the inner reactor 200;
  (c) adding enzymes to the inner reactor 200;
  (d) enzymatically hydrolyzing the cellulose;
  (e) adding distilled water to the inner reactor 200;
  (f) selectively diffusing glucose produced by the enzymatic hydrolysis through the PES membrane 150 from the inner reactor 200 to the outer reactor 300 and to the jacketed glass column 400;
  (g) maintaining the jacketed glass column 400 containing CGTase@H-Cu-BTC at a temperature of about 80° C. while a continuous stream of substantially pure glucose produced by the enzymatic hydrolysis are fed into the jacketed glass column 400;
  (h) reacting the substantially pure glucose with the CGTase enzyme to obtain pure cyclodextrin;
  (i) collecting the substantially pure cyclodextrin; and
  (j) optionally quantifying the cyclodextrin using high performance liquid chromatograph (HPLC),
wherein the enzymatic hydrolysis of cellulose is carried out on a standard cellulose substrate 750,
wherein the enzymatic hydrolysis of cellulose is performed under agitation using a mixer 550 (e.g., magnetic stirrer),
wherein the pH of the enzymatic reaction is about 5.0,
wherein the distilled water is introduced into the inner reactor 200 utilizing a peristaltic pump 700,
wherein the distilled water maintains the enzymatic reaction at a temperature of about 50° C.,
wherein the PES membrane selectively restricts cellulase enzymes and cellulose biomass while letting filtrate glucose,
wherein the jacketed glass column 400 is preloaded with CGTase@H-Cu-BTC 180,
wherein the jacketed glass column 400 is heated by the heating tape 450,
wherein the heating tape 450 is connected to the thermocouple 500, and
wherein the thermocouple 500 is connected to the temperature controller 600.

Embodiment 7. The method of embodiment 6, wherein the mixer 550 (e.g., magnetic stirrer) is agitated at about 450 rpm.

Embodiment 8. The method of embodiment 6, wherein the cyclodextrin produced is selected from the group consisting of cyclomaltohexaose (α-CD), cyclomaltoheptaose (β-CD), and cyclomaltooctaose (γ-CD).

REFERENCES

[1] Szerman, N., Schroh, I., Rossi, A. L., Rosso, A. M., Krymkiewicz, N., & Ferrarotti, S. A. (2007). Cyclodextrin production by cyclodextrin glycosyltransferase from *Bacillus circulans* OF 9R. Bioresource Technology, 98 (15), 2886-2891. See worldwide website: doi.org/10.1016/j.biortech.2006.09.056

[2] Jansook, P., Ogawa, N., & Loftsson, T. (2018). Cyclodextrins: Structure, physicochemical properties and pharmaceutical applications. International Journal of Pharmaceutics, 535 (1), 272-284. See worldwide website: doi.org/10.1016/j.ijpharm.2017.11.018

[3] Liu, Y., Chen, Y., Gao, X., Fu, J., & Hu, L. (2022). Application of cyclodextrin in food industry. Critical Reviews in Food Science and Nutrition, 62 (10), 2627-2640. See worldwide website: doi.org/10.1080/10408398.2020.1856035

[4] da Natividade Schaffer, J., Matte, C. R., Charqueiro, D. S., de Menezes, E. W., Costa, T. M. H., Benvenutti, E. V., Rodrigues, R. C., & Hertz, P. F. (2017). Directed immobilization of CGTase: The effect of the enzyme orientation on the enzyme activity and its use in packed-bed reactor for continuous production of cyclodextrins. Process Biochemistry, 58, 120-127.

[5] Chen, S., Li, Z., Gu, Z., Ban, X., Hong, Y., Cheng, L., & Li, C. (2022). Immobilization of 13-cyclodextrin glycosyltransferase on gelatin enhances 13-cyclodextrin production. Process Biochemistry, 113, 216-223. See worldwide website: doi.org/10.1016/j.procbio.2022.01.005
[6] Ben Amara, F., Bouzid, M., Sahnoun, M., Ben Nasr, Y., Jaouadi, B., Bejar, S., & Jemli, S. (2022). Valorization of Potato Peels Starch for Efficient 13-Cyclodextrin Production and Purification through an Eco-Friendly Process. Starch-Starke, 74 (9-10), 2200037. https://doi.org/10.1002/star.202200037
[7] Ji, H., Bai, Y., Liu, Y., Wang, Y., Zhan, X., Long, J., Chen, L., Qiu, C., & Jin, Z. (2022). Deciphering external chain length and cyclodextrin production with starch catalyzed by cyclodextrin glycosyltransferase. Carbohydrate Polymers, 284, 119156. See worldwide website: doi.org/10.1016/j.carbpol.2022.119156.
[8] Illias, R. M., Tien, S., Rahman, R. A., Rashid, N. A. A., Yusoff, W. W., Hamid, A., Hassan, O., & Kamaruddin, K. (2003). Application of factorial design to study the effects of temperature, initial ph and agitation on the production of cyclodextrin glucanotransferase from alkalophilic *Bacillus* sp. G1. Sci Asia, 29, 135-140.
[9] Sato, M., Yagi, Y., Nagano, H., & Ishikura, T. (1985). Determination of CGTase from *Bacillus ohbensis* and its optimum pH using HPLC. Agricultural and Biological Chemistry, 49 (4), 1189-1191.
[10] Rendleman Jr., J. A. (1997). Enhancement of cyclodextrin production through use of debranching enzymes. Biotechnology and Applied Biochemistry, 26 (1), 51-61. See worldwide website: doi.org/10.1111/j.1470-8744.1997.tb00446.x
[11] Rojas, M. J., Amaral-Fonseca, M., Fernandez-Lafuente, R., de Lima Camargo Giordano, R., & Tardioli, P. W. (2019). Recovery of starch from cassava bagasse for cyclodextrin production by sequential treatment with a-amylase and cyclodextrin glycosyltransferase. Biocatalysis and Agricultural Biotechnology, 22, 101411. See worldwide website: doi.org/10.1016/j.bcab.2019.101411
[12] Muniz, I. de C. B., Santos, J. B., de Oliveira, R. M., Santos, F. G., Souza Junior, E. C. de, Oyama, L., Fontan, R. da C. I., & Bonomo, R. C. F. (2024). Current advances in obtaining novel cyclodextrin glycosyltransferases for optimizing the synthesis of cyclodextrins. Process Biochemistry, 145, 195-209. See worldwide website: doi.org/10.1016/j.procbio.2024.07.008
[13] Ogunbadejo, B. A., & AI-Zuhair, S. (2023). Bioconversion of starch to Cyclodextrin using Cyclodextrin glycosyltransferase immobilized on metal organic framework. Biocatalysis and Agricultural Biotechnology, 53, 102878. See worldwide website: doi.org/10.1016/j.bcab.2023.102878
[14] Ogunbadejo, B. A., Aljahoushi, K. A., Alzamly, A., Greish, Y. E., & AI-Zuhair, S. (2024). Immobilization of Cyclodextrin glycosyltransferase onto three dimensional-hydrophobic and two dimensional-hydrophilic supports: A comparative study. Biotechnology Journal, 19 (1), 2300195. See worldwide website: doi.org/10.1002/biot.202300195
[15] AI-Mardeai, S., Elnajjar, E., Hashaikeh, R., Kruczek, B., Van der Bruggen, B., & AI-Zuhair, S. (2022). Simultaneous Enzymatic Cellulose Hydrolysis and Product Separation in a Radial-Flow Membrane Bioreactor. Molecules, 27 (1), Article 1. See worldwide website: doi.org/10.3390/molecules27010288

What is claimed is:
1. A system for continuous production of cyclodextrins from cellulose or lignocellulosic waste, comprising: a tubular membrane reactor comprising:
(a) an inner reactor;
(b) an outer cylinder surrounding the inner reactor;
(c) an outlet connecting the outer reactor with a jacketed glass column;
(d) a peristaltic pump connected to the inner reactor;
(e) a heating tape fitted with the jacketed glass column via a thermocouple and connected to a temperature controller;
(f) a hierarchical copper-based metal-organic framework (H-Cu-BTC); and
(g) a quantitative filter paper (Grade 40) shredded into standard cellulose substrate having dimensions of about 5×5 mm,
wherein the inner reactor comprises a polyethersulfone (PES) membrane,
wherein the inner reactor is designed for the addition of enzymes, substrates, and lignocellulosic wastes,
wherein the H-Cu-BTC is adapted for CGTase enzyme immobilization, and
wherein the system is useful for the production of cyclodextrins from lignocellulosic wastes or cellulose.

2. The system according to claim 1, wherein the PES membrane has a weight cut-off of about 10 KDa.

3. The system of claim 1, wherein the inner reactor has an internal diameter of about 10 cm and a height of about 19 cm.

4. The system of claim 1, wherein the outer cylinder has an internal diameter of about 15 cm and a height of about 24 cm.

5. The system of claim 1, wherein the jacketed glass column has an internal diameter of about 14 mm, a height of about 78 mm, and a total volume of about 8 mL.

6. A method of using the system of claim 1 for cyclodextrin production, wherein the method comprises:
(a) obtaining cellulose or lignocellulosic waste;
(b) adding the cellulose to the inner reactor;
(c) adding enzymes to the inner reactor;
(d) enzymatically hydrolyzing the cellulose;
(e) adding distilled water to the inner reactor;
(f) selectively diffusing glucose produced by the enzymatic hydrolysis through the PES membrane from the inner reactor to the outer reactor and to the jacketed glass column;
(g) maintaining the jacketed glass column containing CGTase@H-Cu-BTC at a temperature of about 80° C. while a continuous stream of substantially pure glucose produced by the enzymatic hydrolysis are fed into the jacketed glass column;
(h) reacting the substantially pure glucose with the CGTase enzyme to obtain pure cyclodextrin;
(i) collecting the substantially pure cyclodextrin; and
(j) optionally quantifying the cyclodextrin using high performance liquid chromatograph (HPLC),
wherein the enzymatic hydrolysis of cellulose is carried out on a standard cellulose substrate,
wherein the enzymatic hydrolysis of cellulose is performed under agitation using a mixer,
wherein the pH of the enzymatic reaction is about 5.0,
wherein the distilled water is introduced into the inner reactor utilizing a peristaltic pump,
wherein the distilled water maintains the enzymatic reaction at a temperature of about 50° C.,
wherein the PES membrane selectively restricts cellulase enzymes and cellulose biomass while letting filtrate glucose,
wherein the jacketed glass column is preloaded with CGTase@H-Cu-BTC, wherein the jacketed glass column is heated by the heating tape, wherein the heating tape is connected to the thermocouple, and wherein the thermocouple is connected to the temperature controller.

7. The method of claim 6, wherein the mixer is agitated at about 450 rpm.

8. The method of claim 6, wherein the cyclodextrin produced is selected from the group consisting of cyclomaltohexaose (α-CD), cyclomaltoheptaose (β-CD), and cyclomaltooctaose (γ-CD).

* * * * *